United States Patent
Whipple et al.

(10) Patent No.: US 9,358,057 B1
(45) Date of Patent: Jun. 7, 2016

(54) SACROILIAC SCREW

(71) Applicant: Amendia, Inc., Marietta, GA (US)

(72) Inventors: Dale Whipple, Acworth, GA (US); Jason Hayes Tillett, Atlanta, GA (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 14/630,748

(22) Filed: Feb. 25, 2015

(51) Int. Cl.
| | |
|---|---|
| A61B 17/86 | (2006.01) |
| A61B 17/70 | (2006.01) |
| A61B 17/16 | (2006.01) |
| A61B 17/84 | (2006.01) |
| A61B 17/88 | (2006.01) |
| A61B 17/56 | (2006.01) |
| A61B 17/17 | (2006.01) |

(52) U.S. Cl.
CPC ........... *A61B 17/864* (2013.01); *A61B 17/1637* (2013.01); *A61B 17/56* (2013.01); *A61B 17/7055* (2013.01); *A61B 17/84* (2013.01); *A61B 17/86* (2013.01); *A61B 17/861* (2013.01); *A61B 17/8605* (2013.01); *A61B 17/8615* (2013.01); *A61B 17/8625* (2013.01); *A61B 17/8635* (2013.01); *A61B 17/8685* (2013.01); *A61B 17/88* (2013.01); *A61B 17/8805* (2013.01); *A61B 17/1757* (2013.01); *A61B 2017/564* (2013.01); *A61B 2017/8655* (2013.01)

(58) Field of Classification Search
CPC ............. A61B 17/56; A61B 2017/564; A61B 17/7055; A61B 17/84; A61B 17/86; A61B 17/8605; A61B 17/861; A61B 17/8615; A61B 17/8625; A61B 17/8635; A61B 17/864; A61B 2017/8655; A61B 17/8685; A61B 17/88; A61B 17/8805
See application file for complete search history.

(56) References Cited

U.S. PATENT DOCUMENTS

| | | | |
|---|---|---|---|
| 6,019,760 A | 2/2000 | Metz-Stavenhagen et al. | |
| 6,053,916 A | 4/2000 | Moore | |
| 6,402,757 B1* | 6/2002 | Moore, III | A61B 17/862 606/104 |
| 6,635,059 B2 | 10/2003 | Randall et al. | |
| 8,529,609 B2 | 9/2013 | Helgerson et al. | |
| 8,808,377 B2 | 8/2014 | Donner | |
| 8,894,685 B2 | 11/2014 | Mickiewicz et al. | |
| 2006/0155286 A1 | 7/2006 | Wang | |
| 2007/0233123 A1* | 10/2007 | Ahmad | A61B 17/863 606/307 |
| 2009/0192551 A1 | 7/2009 | Cianfrani et al. | |
| 2010/0211113 A1* | 8/2010 | Olson | A61B 17/8625 606/301 |
| 2011/0137352 A1* | 6/2011 | Biedermann | A61B 17/8635 606/305 |
| 2011/0190830 A1 | 8/2011 | Biedermann | |
| 2012/0095515 A1* | 4/2012 | Hamilton | A61B 17/864 606/304 |
| 2012/0197311 A1 | 8/2012 | Kirschman | |
| 2012/0323285 A1* | 12/2012 | Assell | A61B 17/8625 606/305 |

(Continued)

FOREIGN PATENT DOCUMENTS

CN 102793579 11/2012

*Primary Examiner* — Larry E Waggle, Jr.
(74) *Attorney, Agent, or Firm* — David L. King

(57) ABSTRACT

An improved joint fusion screw for transiliac fixation has an elongate hollow shaft. The hollow shaft has an externally threaded end portion extending to a tip end and a non-externally threaded shank portion having openings. The tip end has at least two bone cutting flutes at the bottom of the shaft. Each bone cutting flute has a cutting edge on a circumferential exterior of the threaded tip to cut bone and direct the cut bone internally into the hollow shaft toward the shank.

24 Claims, 4 Drawing Sheets

(56) References Cited

U.S. PATENT DOCUMENTS

| 2013/0018427 A1 | 1/2013 | Pham et al. |
| 2014/0121707 A1 | 5/2014 | Stark |
| 2014/0257409 A1* | 9/2014 | Reed ............... A61B 17/864 606/304 |
| 2014/0277188 A1* | 9/2014 | Poulos ............. A61B 17/1655 606/304 |

* cited by examiner

SACROILIAC SCREW

TECHNICAL FIELD

The present invention relates to an improved spinal fixation screw for transiliac fixation and a method of use.

BACKGROUND OF THE INVENTION

Many complaints of lower back pain and leg pain have been attributed to herniated discs or other injuries to the spinal column. Extensive therapy and treatment has often been unsuccessful in alleviating such pain. It has been established that some of this lower back and leg pain can be attributed to symptomatic sacroiliac dysfunction or instability. Normally, the sacroiliac joint which spans between the sacrum bone and ilium bone has nutation of one to two degrees. "Nutation" is the medical term which describes the relative movement between the sacrum and ilium. A patient's sacroiliac joint can become damaged resulting in hypermobility of the joint. Because of the small range of motion in the sacroiliac joint, hypermobility is very difficult to diagnose. Therefore, lower back pain or leg pain caused by sacroiliac dysfunction often goes misdiagnosed or undiagnosed.

Accordingly, it is an objective of this invention to provide a device for correcting symptomatic sacroiliac dysfunction or instability. It is another aspect of this invention to provide a device which enhances stability and compression for purposes of immobilizing a joint, and for fusing two opposed bone structures across the joint.

SUMMARY OF THE INVENTION

An improved joint fusion screw for transiliac fixation has an elongate hollow shaft. The hollow shaft has an externally threaded end portion extending to a tip end and a non-externally threaded shank portion having a plurality of openings. The tip end has at least two bone cutting flutes at the bottom of the shaft. Each bone cutting flute has a cutting edge on a circumferential exterior of the threaded tip to cut bone and direct the cut bone internally into the hollow shaft toward the shank. Each cutting edge lies in a plane parallel to an axis of the elongate hollow shaft.

In each embodiment, the hollow shaft has a bone chamber for receiving the cut bone fragments. The bone chamber extends to at least the openings of the shank portion. Autograft cut bone fragments are directed to the openings to enhance new bone growth and rapid fusion of the fusion screw. Preferably, the openings of the shank portion are elongated slots.

The screw has an enlarged flat head affixed or integral to an end of the shank. The end of the shank portion has internal or female threads for receiving a threaded driver cap. The threaded driver cap has a cannulated opening or aperture for passing a guide wire and a torquing tool receiving cavity to thread the screw into the bone. The drive cap is affixed into the threaded end of the shank. The driver cap can be removably attached to allow bone packing material to be packed into the hollow shaft after screw insertion into the bone. The at least two cutting flutes are preferably diametrically opposed.

In one embodiment, each bone cutting flute has an arcuate ramp extending from the cutting edge toward an inside diameter of the hollow shaft. The cut bone fragments are directed internal along the arcuate ramps upon implantation of the screw into the hollow shaft. Each of the cutting edges form spiral cut autograft bone upon screw implantation. Each of the formed spiral cut autograft bone remains connected by tissue to increase osteoconductivity.

In a second embodiment, the at least two cutting flutes extend starting from the tip end longitudinally through two or more threads.

In a third embodiment, the tip end can have a web or bridge extending across the hollow shaft. The web or bridge has an aperture for receiving a guide wire. The aperture is coaxial with an axis of the screw and the aperture of the cap driver.

A method of transiliac fixation using the improved screw comprises the steps of pre-drilling an opening in the sacrum and the ilium bones to be fixed with a pilot hole opening and inserting a joint fixation screw with a hollow shaft onto the pre-drilled opening while cutting autograft bone fragments directed into the hollow shaft. The hollow shaft has a bone receiving chamber extending to a plurality of openings further in the hollow shaft and the step of threading of the screw directs the autograft bone fragments to the openings to enhance fusion. The screw can have apertures at the tip end and at the driver cap and the method may further comprise the steps of inserting a guide wire to create a drill path, inserting a cannulated drill over the guide wire to pre-drill the pilot hole, and then inserting the screw onto the guide wire to direct the path for insertion into the bone.

BRIEF DESCRIPTION OF THE DRAWINGS

The invention will be described by way of example and with reference to the accompanying drawings in which.

DETAILED DESCRIPTION OF THE INVENTION

Figure 1:
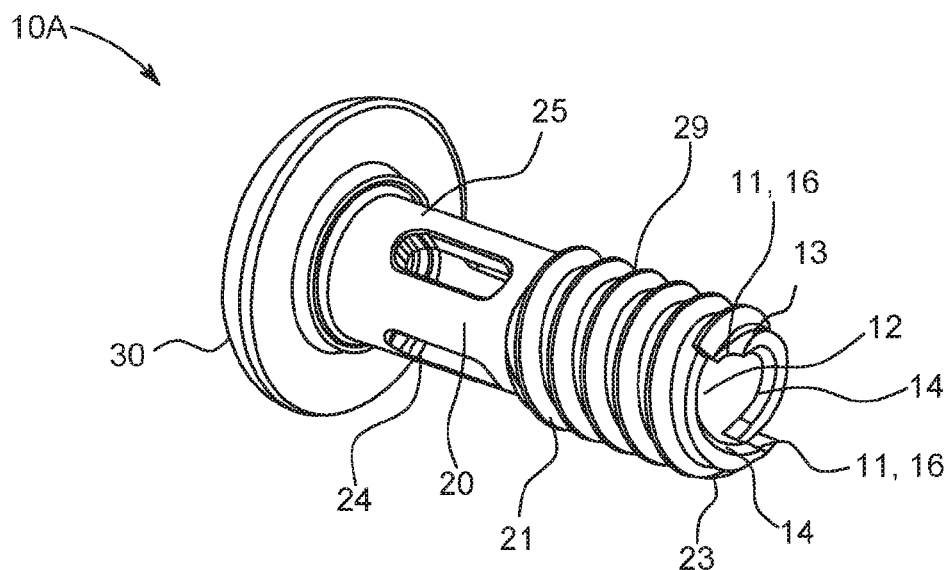
FIG. 1 is a perspective view of a first embodiment of the present invention.
Figure 2:
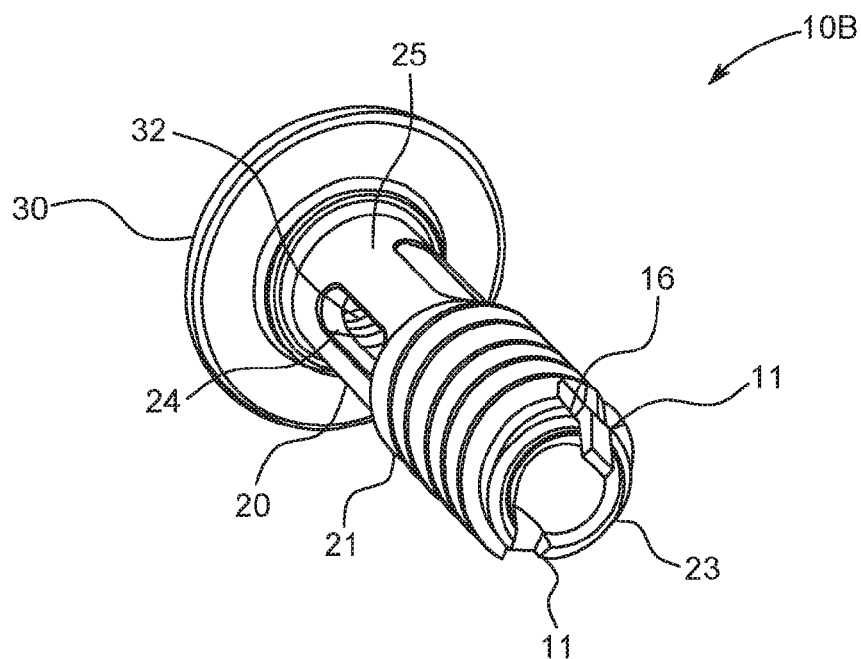
FIG. 2 is a perspective view of a second embodiment of the present invention.
Figure 3:
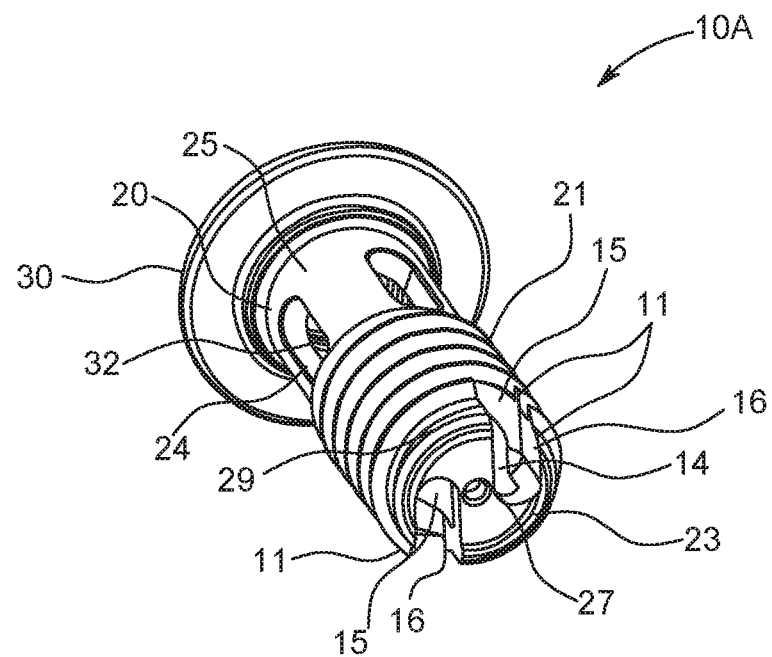
FIG. 3 is a perspective view of a third embodiment of the present invention.
Figure 4:
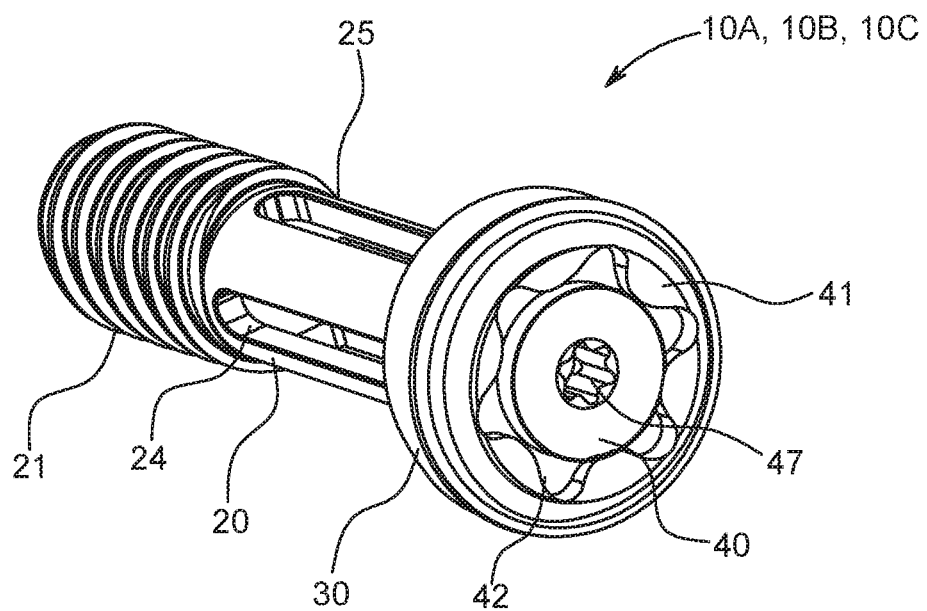
FIG. 4 is an opposite end perspective view for each of the aforementioned embodiments.

With reference to FIGS. 1, 2 and 3, three versions or embodiments of an improved joint fixation screw 10A, 10B and 10C for a transiliac fixation are shown. Each embodiment has common features with variations on the cutting flutes and tip end design. FIG. 4 shows the proximal head end opposite to the bone cutting tip end. The head 30 at this end is a common feature to all three embodiments.

Each screw 10A, 10B and 10C has a hollow elongated shaft 20. The shaft 20 has an externally threaded end portion 21 and a smooth shank portion 25. The smooth shank portion 25 has a plurality of openings 24 open to a chamber 12 inside the hollow shaft 20. At a proximal end of the screws 10A, 10B and 10C is an enlarged head 30. The center of the head 30 is a threaded opening 32 open to the chamber 12. The threaded end portion 21 of the hollow shaft 20 has threads 29. All these features are common to each screw 10A, 10B and 10C.

In a first embodiment of FIG. 1, the screw 10A has two cutting flutes 11. Each flute 11 is diametrically opposed from the other and each has a cutting edge 13 formed from a leading thread 29 at the tip end 21. The cutting edges 13 lie in a plane parallel to the axis of the screw shaft and each had an arcuate ramp 14 for directing bone fragments into the hollow chamber 12. The cut fragments spiral into the chamber 12 along the ramped surfaces 14.

In a second embodiment of FIG. 2, each of the cutting flutes 11 extend deeper across two or more threads 29 of the end portion 21 to a bottom 16. The cutting edges 13 are still circumferentially in a plane parallel to the axis, but the deep longitudinally extending opening of the flutes 11 captures the cut bone fragments and directs them into the chamber 12 in pieces that are broken on threading.

With reference to FIG. 3, a third embodiment, a bridge or web 23 extends across the hollow shaft 20 at the tip end 21 defining a pair of openings 15 between the bridge or web 23 and the flutes 11, as shown. The bridge or web 23 has an aperture 27 for receiving a guide wire. This third version screw 10C has the same flutes 11 as shown in FIG. 2.

FIG. 4, shows a threaded driver cap 40 inserted and threaded into the threads 32 of the enlarged head 30. This driver cap 40 has a torque receiving cavity 41 with projections 42 to receive a torquing tool to implant the screw 10A, 10B or 10C. Centrally, there is an aperture 47 to allow the screw 10C to pass over a guide wire along a directional pre-drilled path.

As the screw 10A, 10B or 10C is torqued into the pre-drilled pilot hole, the cutting flutes 11 create autograft bone fragments that are delivered directly into the chamber 12. In this way, the patient's bone fragments are made available to enhance new bone growth to fuse the screw 10A, 10B or 10C in place.

One purpose of this invention is to direct bone that is cut by the self-tapping threads and cutting edges 13 at the tip of the bone screw 10A, 10B or 10C or otherwise gathered by the flutes 11 into the internal chamber 12 of the screw to serve as additional autograft material. Previously, this material would be compressed into the bone around the outside of the screw. The screw would be filled with previously harvested autograft material which could be packed into the screw from an opening in the head end of the screw. The screw is used to secure two bones together, in this case the sacrum and the ilium. When preparing the bone to accept the screw, a hole will be drilled and tapped to a size smaller than the actual screw. The screw can be packed with graft material prior to implantation. The self-tapping edge of the screw will cut additional autograft material as it is installed and the flute will direct this freshly cut autograft material to join the existing material in the inner chamber 12 of the screw. Some of this material will be pushed out of the plurality of openings 24 or fenestrations in the shaft 20 of the screw as it is tightened to aid in fusion around and into the body of the screw. Many variations of similar flute shapes will produce a similar result. The screw material can be anything hard and strong enough to cut and direct bone chips and withstand the biomechanical loads of the application, preferably titanium, stainless steel or alloys of these materials or metals will work satisfactorily.

Figure 5:
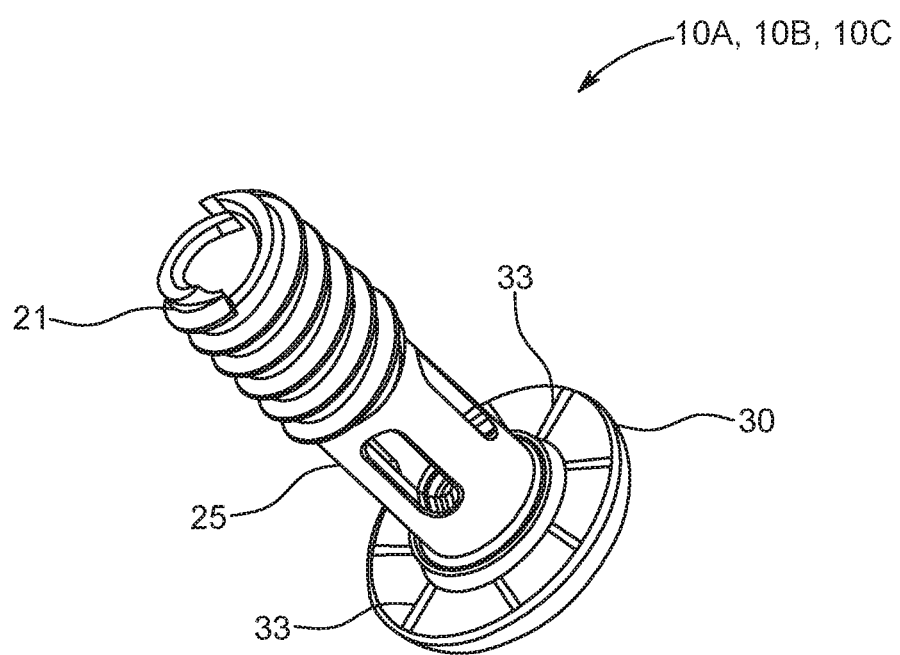
FIG. 5 shows the optional anti-back out feature on the head.

The present invention SI (Sacro-iliac) screw described herein has shown several important features of this screw. These features include: the lagging where the head 30 is pulled down by the coarse threads 29 and the lagged portion is within the smooth shank portion 25 and not engaged by threads 29; the screw has a large bore or chamber 12 for inserting bone graft with the option to cap this bore which communicates to the SI space after insertion with the driver cap 40; the shaft 20 has only the single threaded end portion 21 to engage only the sacrum bone, the ilium bone is positioned on the smooth shank portion 25; an optional anti-back out feature under the head 30 in the form of a series of wedge-shaped teeth 33 to engage the iliac bone surface can be used as shown in FIG. 5. A wedge shaped washer (not shown) could be used under the screw head 30 to accommodate the surface angle of the ilium with respect to the screw axis and also employ the anti-back out feature shown in FIG. 5, but as a separate washer piece.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An improved joint fusion screw for transiliac fixation comprising:
   an elongate hollow shaft, the hollow shaft having an externally threaded end portion extending to a tip end and a non-externally threaded shank portion having a plurality of openings; and
   wherein the tip end has at least two bone cutting flutes at a bottom of the shaft, each bone cutting flute having a cutting edge on a circumferential exterior of a threaded tip to cut bone and direct the cut bone internally into the hollow shaft toward the shank, each cutting edge lies in a plane parallel to an axis of the elongate hollow shaft, each bone cutting flute has an arcuate ramp extending from the cutting edge toward an inside diameter of the hollow shaft.

2. The improved joint fusion screw for transiliac fixation of claim 1 wherein cut bone fragments are directed internal along the arcuate ramps upon implantation of the screw into the hollow shaft.

3. The improved joint fusion screw for transiliac fixation of claim 1 wherein the openings of the shank portion are elongated slots.

4. The improved joint fusion screw for transiliac fixation of claim 1 wherein the screw has an enlarged flat head affixed or integral to an end of the shank portion.

5. The improved joint fusion screw for transiliac fixation of claim 1 wherein a driver cap is removably attached to allow bone packing material to be packed into the hollow shaft after insertion into the bone.

6. The improved joint fusion screw for transiliac fixation of claim 1 wherein the at least two cutting flutes are diametrically opposed.

7. The improved joint fusion screw for transiliac fixation of claim 1 wherein the at least two cutting flutes extend starting from the tip end longitudinally through two or more threads.

8. The improved joint fusion screw for transiliac fixation of claim 1 wherein the tip end has a web or bridge extending across the hollow shaft, the web or bridge having an aperture for receiving a guide wire.

9. The improved joint fusion screw for transiliac fixation of claim 8 wherein the aperture is coaxial with an axis of the screw.

10. An improved joint fusion screw for transiliac fixation comprising:
    an elongate hollow shaft, the hollow shaft having an externally threaded end portion extending to a tip end and a non-externally threaded shank portion having a plurality of openings; and
    wherein the tip end has at least two bone cutting flutes at a bottom of the shaft, each bone cutting flute having a cutting edge on a circumferential exterior of a threaded tip to cut bone and direct the cut bone internally into the hollow shaft toward the shank, the hollow shaft has a bone chamber for receiving the cut bone, the bone chamber extending to at least the openings of the shank portion, autograft cut bone fragments are directed to the openings to enhance new bone growth and fusion of the fusion screw, each of the cutting edges form spiral cut autograft bone upon screw implantation.

11. The improved joint fusion screw for transiliac fixation of claim 10 wherein each of the formed spiral cut autograft bone remains connected by tissue to increase osteoconductivity.

12. An improved joint fusion screw for transiliac fixation comprising:
   an elongate hollow shaft, the hollow shaft having an externally threaded end portion extending to a tip end and a non-externally threaded shank portion having a plurality of openings; and
   wherein the tip end has at least two bone cutting flutes at a bottom of the shaft, each bone cutting flute having a cutting edge on a circumferential exterior of a threaded tip to cut bone and direct the cut bone internally into the hollow shaft toward the shank, an end of the shank portion has internal or female threads for receiving a threaded driver cap; and
   wherein the threaded driver cap has a cannulated opening or aperture for passing a guide wire and a torquing tool receiving cavity to thread the screw into the bone and is affixed into the threaded end of the shank portion.

13. A method of transiliac fixation comprises the steps of:
   pre-drilling an opening in a sacrum and an ilium bone to be fixed with a pilot hole opening;
   inserting a joint fixation screw with a hollow shaft onto the pre-drilled opening while cutting autograft bone fragments directed into the hollow shaft; and
   wherein the hollow shaft has a bone receiving chamber extending to a plurality of openings further in the hollow shaft and the method further comprises a step of threading the screw into the openings in the bones thereby directing the autograft bone fragments to the openings to enhance fusion.

14. The method of transiliac fixation of claim 13 wherein the screw has an aperture at a tip end and a driver cap and the method further comprises the steps of:
   inserting a guide wire to create a drill path;
   inserting a cannulated drill over the guide wire to pre-drill the hole; and
   inserting the screw onto the guide wire to direct the path for insertion into the bone.

15. An improved joint fusion screw for transiliac fixation comprising:
   a screw head;
   an elongate hollow shaft, the hollow shaft having an externally threaded end portion having threads extending to a tip end and a non-externally threaded shank portion having a plurality of openings; and wherein the tip end has at least two bone cutting flutes; and
   wherein upon tightening the screw, the threads in the threaded end portion are configured to engage a sacrum bone and the screw head pulls an ilium bone towards the sacrum bone, each cutting flute having a cutting edge that lies in a plane parallel to an axis of the elongate hollow shaft, each bone cutting flute has an arcuate ramp extending from the cutting edge toward an inside diameter of the hollow shaft.

16. The improved joint fusion screw for transiliac fixation of claim 15 wherein the hollow shaft has a bone chamber for receiving bone fragments, the bone chamber extending to at least the openings of the shank portion.

17. The improved joint fusion screw for transiliac fixation of claim 16 wherein autograft cut bone fragments are directed to the openings to enhance new bone growth and fusion of the fusion screw.

18. The improved joint fusion screw for transiliac fixation of claim 15 wherein the openings of the shank portion are elongated slots.

19. The improved joint fusion screw for transiliac fixation of claim 15 wherein the head of the screw is an enlarged flat head affixed or integral to an end of the shank portion.

20. The improved joint fusion screw for transiliac fixation of claim 15 wherein an end of the shank portion has internal or female threads for receiving a threaded driver cap.

21. The improved joint fusion screw for transiliac fixation of claim 20 wherein the threaded driver cap has a cannulated opening or aperture for passing a guide wire and a torquing tool receiving cavity to thread the screw into the bone and is affixed into the threaded end of the shank portion.

22. The improved joint fusion screw for transiliac fixation of claim 15 wherein a driver cap is removably attached to allow bone packing material to be packed into the hollow shaft after insertion into the bone.

23. The improved joint fusion screw for transiliac fixation of claim 15 wherein the at least two bone cutting flutes are diametrically opposed to the other.

24. The improved joint fusion screw for transiliac fixation of claim 23 wherein the at least two cutting flutes extend starting from the tip end longitudinally through two or more threads.

* * * * *